United States Patent [19]
Barton et al.

[11] Patent Number: 5,221,268
[45] Date of Patent: Jun. 22, 1993

[54] MULTIPLE DOSE CONTROL APPARATUS

[75] Inventors: Russell C. Barton, Carlsbad; Maresala Milo, San Diego; Charles N. Bunn, Escondido, all of Calif.

[73] Assignee: Block Medical, Inc., Carlsbad, Calif.

[21] Appl. No.: 804,837

[22] Filed: Dec. 6, 1991

[51] Int. Cl.$^5$ .............................................. A61M 5/00
[52] U.S. Cl. ................................. 604/250; 604/132; 604/246; 251/7
[58] Field of Search ................ 604/65, 67, 132, 153, 604/246, 249, 250; 128/DIG. 13; 251/4, 7

[56] References Cited

U.S. PATENT DOCUMENTS

| | | | |
|---|---|---|---|
| 3,993,069 | 11/1976 | Buckles et al. | 604/132 |
| 4,191,184 | 3/1980 | Carlisle | 604/246 |
| 4,493,710 | 1/1985 | King et al. | 604/250 |
| 4,553,958 | 11/1985 | Le Cocq | 604/246 |
| 4,626,241 | 12/1986 | Campbell et al. | 604/250 |
| 4,634,426 | 1/1987 | Kamen | 604/65 |
| 4,878,646 | 11/1989 | Edelman et al. | 604/250 |

Primary Examiner—John D. Yasko
Assistant Examiner—Anthony Gutowski
Attorney, Agent, or Firm—Baker, Maxham, Jester & Meador

[57] ABSTRACT

A multiple dose infusion controller for controlling the delivery of multiple dosages of an intravenous fluid from a source to a site comprises a compact, portable housing having a slot for removably receiving a segment of a disposable tubing connected to an IV source for transporting an IV fluid to a site, a valve member mounted in the housing for periodically engaging and compressing the tubing for closing the tubing for preventing flow of fluid therethrough, a motor in the housing for driving the valve member upon energization to selected open and closed positions, and controls in the housing for periodically energizing the motor for selectively controlling the flow of the fluid through the tubing in accordance with predetermined delivery times and duration parameters.

14 Claims, 4 Drawing Sheets

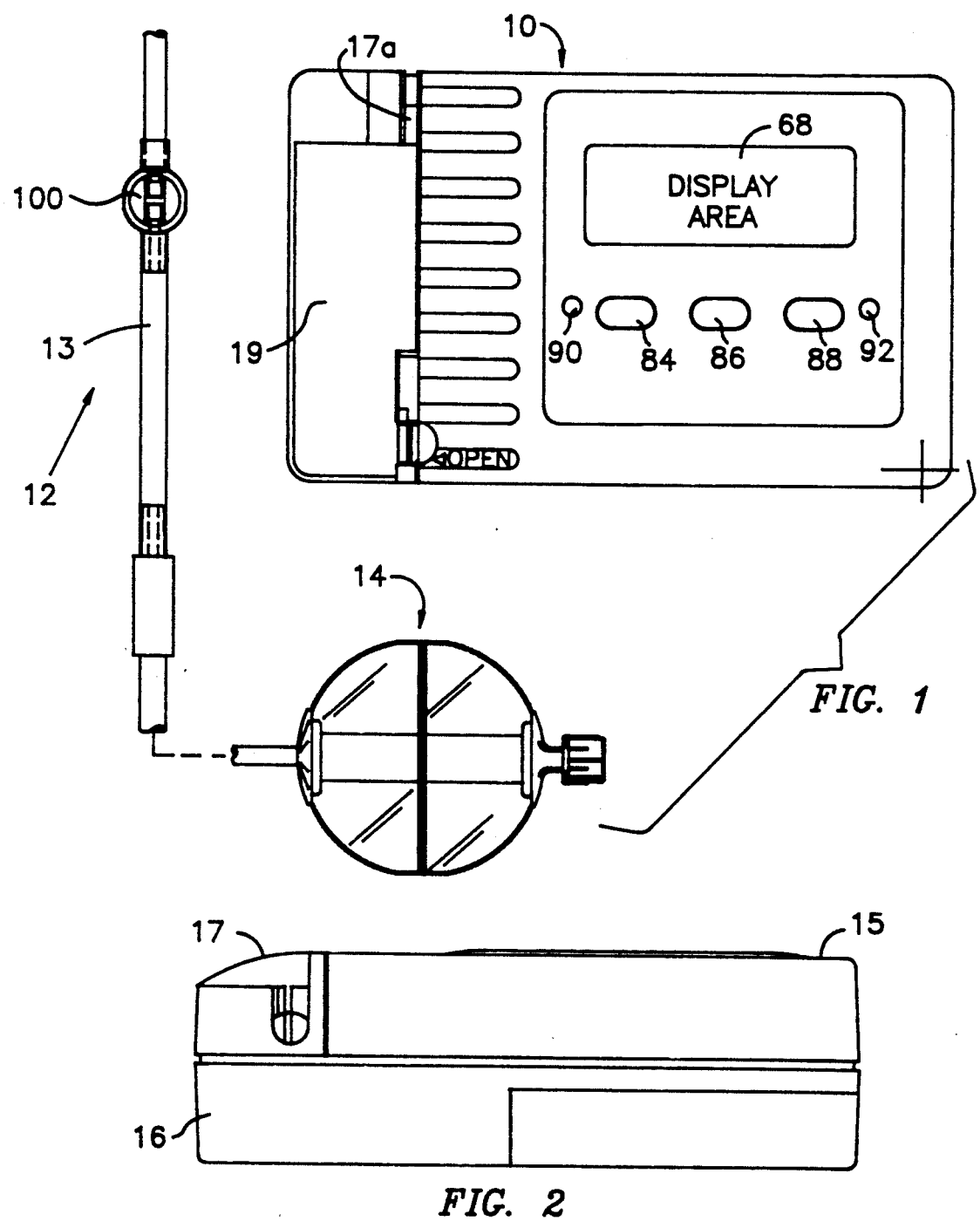

MULTIPLE DOSE CONTROL APPARATUS

BACKGROUND OF THE INVENTION

The present invention relates to medical devices, and more particularly, to an improved multiple dose infusion controller for delivering multiple doses of intravenous drugs at selected intervals at a controlled rate to a patient.

There is an ever increasing desire in the health care field to get patients out of expensive hospital care environments and back to their homes. Many such patients require intravenously administered medications, but are unable to afford the expensive equipment necessary to administer the medication in the prescribed manner.

It is often necessary to intravenously supply patients with multiple doses of pharmaceutically active liquids over a long period of time at a controlled rate. It is desirable that this be accomplished while the patient is in an ambulatory state. It is also desirable that the infusion system incorporate means for keeping the veins of the patient open between periods of infusion.

The prior art includes devices that employ a bag filled with fluid medication that feeds by gravity through IV tubing having drip or other controllers. It is difficult for a patient to be ambulatory with a gravity fed infusion device. In addition, flow control in this type of device is typically manual and very limited.

Another prior art infusion apparatus comprises an elastic bladder forming a liquid container, an elongated cylindrical housing enclosing the bladder, a flow control valve, and tubing for supply of the liquid to the patient. The elastic walls of the bladder expand along the walls of the cylindrical housing when filled with the liquid, and provide the pressure for expelling the liquid. While such devices are suitable for ambulatory use, the flow control is usually manually operated valves or clips and very limited.

Attempts have been made to control pressure and flow rates in many of these devices by means of complicated and expensive flow control valves and devices. Other approaches have utilized exotic and expensive elastic materials in an effort to control the pressures and flow rates.

Another type of infusion apparatus uses pressurized gas as the driving force for the intravenous liquid. In such systems, there may be hydraulic feedback through the pneumatic source in order to precisely regulate hydraulic pressure. See for example U.S. Pat. Nos. 4,430,078 of Sprague, 4,335,835 of Beigler et al., and 4,327,724 of Birk et al.

Still another type of infusion apparatus employs a peristaltic or other positive displacement pump which is electrically driven. Programmable infusion pumps have been provided having the capability for precise tailoring of the fluid delivery rate parameters in different modes, such as continuous, intermittent, PCA (patient controlled analgesic) and TPN (total parenteral nutrition). Originally, such programmable infusion pumps were large and not well suited for ambulatory patients. They used complex and expensive replacement pump cartridges to maintain sterility.

More recently, small programmable infusion pumps have been available with disposable plastic cartridges that engage a peristaltic pump. However, a major drawback of existing programmable infusion systems of this type is that they are complicated and very expensive to manufacture and to maintain.

A recently developed inflatable bladder infusion device has many desirable characteristics for inexpensive ambulatory use. The device has a highly uniform pressure and flow rate and is inexpensive to manufacture and use. However, it lacks the necessary control to provide multiple dosages with means to keep the vein open.

Accordingly, it would be desirable to provide an improved low cost multiple dose controller for use with inexpensive infusion systems for delivering intravenous drugs in selected multiple doses at a controlled rate to an ambulatory patient that can be more easily programmed by a patient, and which will allow patient verification of the prescribed delivery parameters.

SUMMARY OF THE INVENTION

It is, therefore, the primary object of the present invention to provide an improved low cost programmable multiple dosage controller for a disposable infusion pump for an ambulatory patient which enables intravenous fluid delivery parameters to be readily programmed and verified by the patient.

A primary aspect of the invention comprises a programmable multiple dose controller for an infusion system, which includes a disposable infusion device and tubing for conveying intravenous fluid from a source to a patient. The controller comprises a compact, portable housing having a receptacle slot for removably receiving a segment of the disposable tubing. A fixed stroke pinching apparatus is mounted in the housing, with a finger for engaging the segment of the disposable tubing for selectively controlling the flow of intravenous fluid therethrough. A motor is mounted in the housing and is connected for driving the pinching finger upon energization thereof. A keyboard provides user interface with a volume key for selecting the volume.

BRIEF DESCRIPTION OF THE DRAWINGS

The above and other objects and advantages of the present invention will become apparent from the following description when read in conjunction with the accompanying drawings wherein:

FIG. 1 is a front elevation view of a preferred embodiment of the invention;

FIG. 2 is a side elevation view;

DETAILED DESCRIPTION OF A PREFERRED EMBODIMENT

Figure 3:
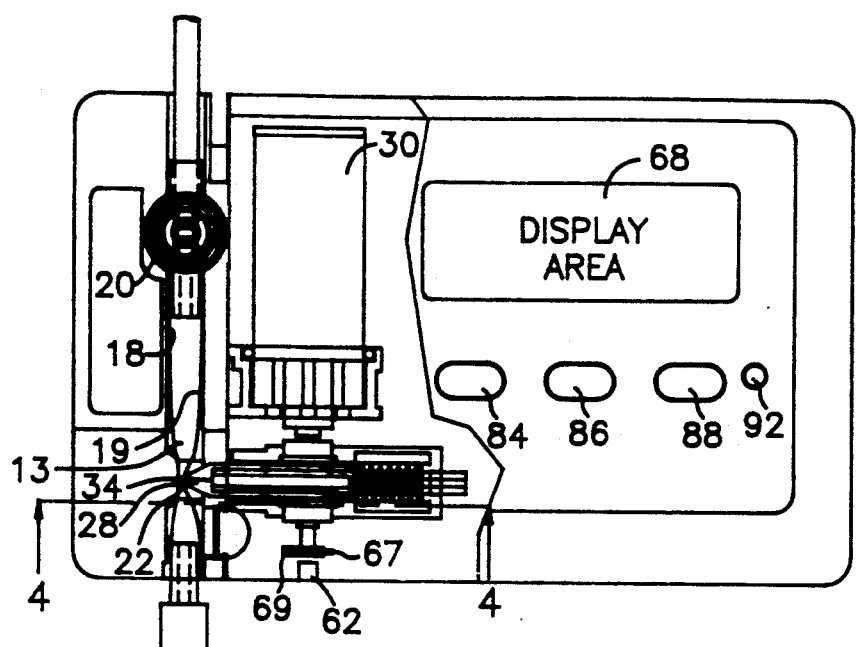
FIG. 3 is a partial view like FIG. 1 with portions broken away to reveal details.

The present invention is directed to a flow controller for controlling the flow from a pressurized source of fluid to an IV injection site to provide multiple dosages and to provide periodic injections to keep the veins of the patient open. Referring particularly to FIG. 1, a controller in accordance with the invention, designated generally by the numeral 10, is shown for receiving a disposable IV tubing unit 12 having an elastic section 13 and extending from a pressurized infusion device, designated generally by the numeral 14, for controlling the flow of IV fluid to an injection site, such as an IV needle or the like. The flow controller unit 10 comprises a generally rectangular box-like housing formed of upper and lower half-shells 15 and 16 having an internal chamber in which is mounted an electronics control system and drive means for activating or controlling an occlusion control valve to be described.

The front or upper face of the housing is formed with an upwardly opening slot, as shown in FIGS. 3, with opposed side walls 18 and 19 extending completely across the face of the unit and open at the ends thereof to the sides of the housing of the control unit. A cover or door 17 is hinged at 17a to the housing and pivots toward and away from the slot to cover it and retain the tubing unit 12 therein. This slot receives the elastic section 13 of the tubing unit 12, and the controller controls the flow of fluid therethrough in a programmed manner, as will be subsequently described.

The slot is formed of vertically extending side walls 18 and 19, which arc outward at or toward an outlet end to form a generally cylindrical cavity 20 for receiving and mounting an occlusion drum 100 for activating a detector, such as disclosed in U.S. Pat. No. 5,078,683, granted Jan. 7, 1992.

The wall 18 bulges inward near the inlet end of the slot forming a platen surface 22 against which the tubing section 13 of the disposable unit 12 is pinched. An opening 24 formed in the wall 19 allows the passage of a reciprocably mounted elongated slide or finger 26 having a wedge tip 28 for engaging and pinching a tube disposed within the slot 18. The finger 26 and platen 22 act on the elastic section 13 of the disposable unit 12 and function as and may be referred to as a pinch valve.

Figure 4:
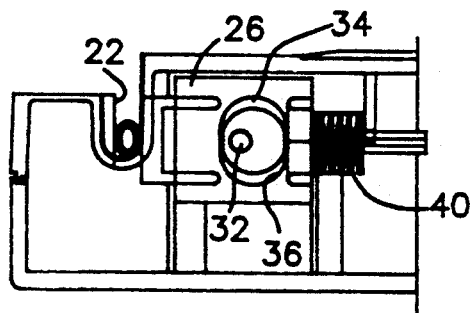
FIGS. 4-6 are views taken on line 4—4 of FIG. 3.
Figure 5:
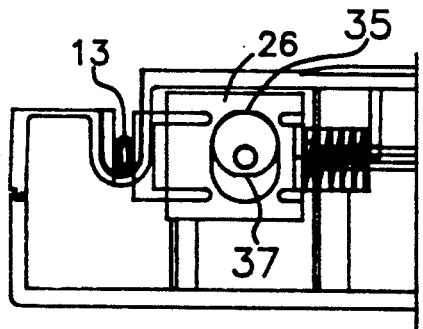
Figure 6:
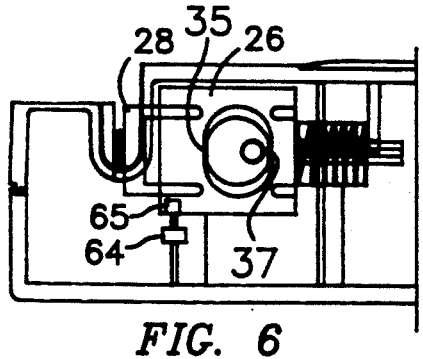

Referring to FIGS. 3–6, a portion of the housing is broken away to illustrate the drive motor and drive mechanism for the pinch valve. The drive mechanism comprises a DC rotary motor 30 having a rotating shaft 32 on which is mounted an eccentric disk or cam 34. The eccentric disk extends into a slot 36 formed in the main portion of the finger 26 as shown in FIGS. 4–6. This basically forms an eccentric and yoke drive mechanism for driving the finger away from the pinched position. The disk 34 is formed with flats 35 and 37 at the maximum and minimum displacement positions. These are engaged by the surface of the slot 36, and act as a detent to hold the drive in the respective open and closed positions when centered at maximum or minimum displacement. A spring 40 of the compression coil type biases against the outer end of the finger member 26 and biases it to the pinched or occluded position of FIG. 6. It also forces the surfaces of the slot against the flats of the eccentric 34.

The drive mechanism includes the spring 40, which functions to drive the finger 26 to engage and compress the tube, and the motor, and the eccentric and slot function to pull the finger away from the elastic infusion tube 13 of the disposable tube unit 12. The finger forms occlusion means for compressing and occluding the infusion tubing (FIG. 6) to stop the flow of fluid and to pull away from it (FIG. 3) to allow the flow of fluid. The finger in combination with the opposed platen 22 functions as a very controlled pinch valve as will be explained.

The controller is designed to be used in conjunction with any suitable infusion apparatus, such as disclosed in U.S. Pat. No. 5,080,652, granted Jan. 14, 1992, and entitled "Infusion Apparatus", and assigned to the assignee hereof, is incorporated herein by reference as though fully set forth. This combination provides a low cost and effective multiple dose infusion system.

Figure 7:
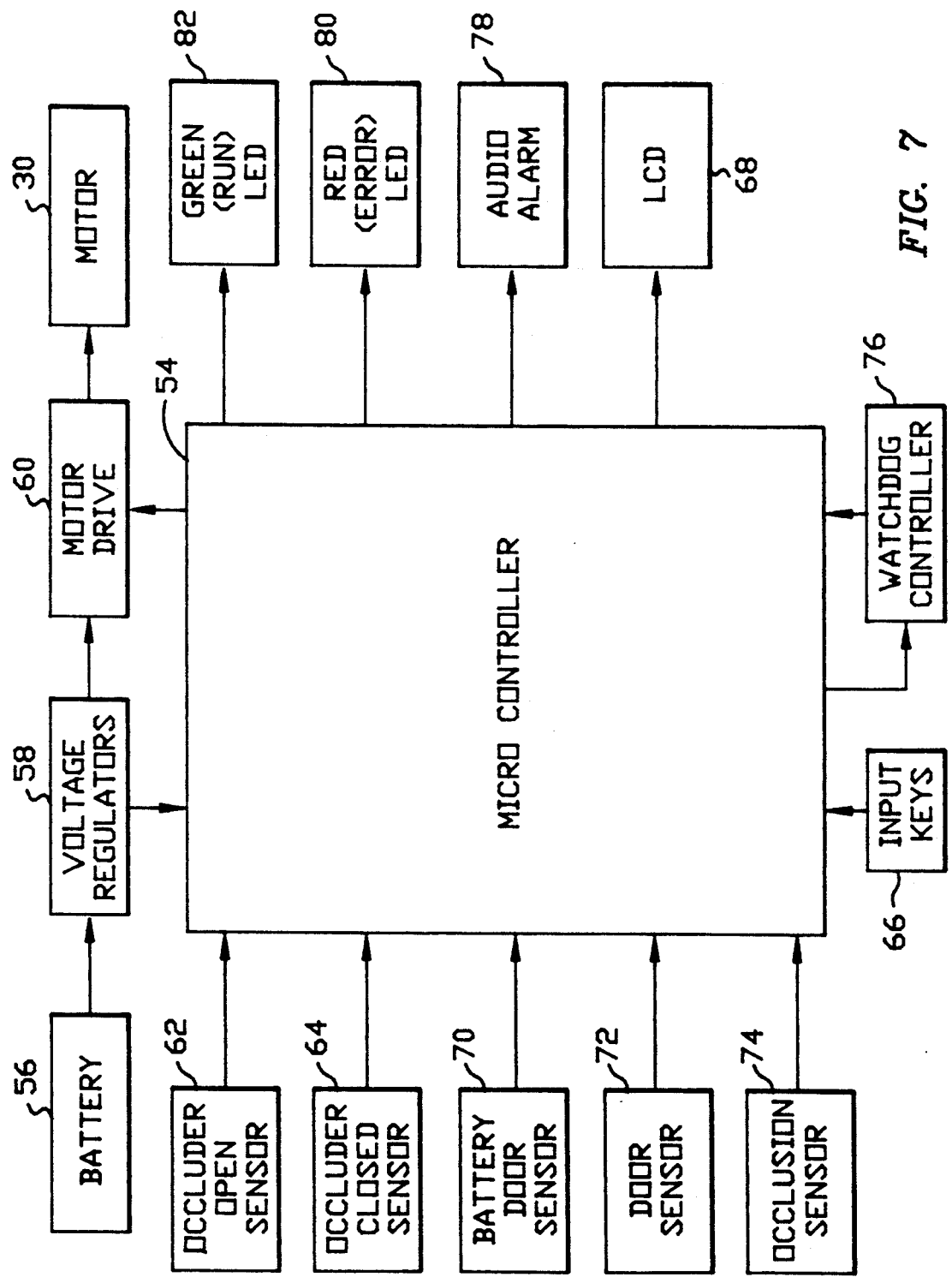
FIG. 7 is a block diagram of the system of FIG. 1.

Referring to FIG. 7, a control system for controlling the drive motor for the pinch valve and for the other electronics of the system is illustrated. The control system has some common features and components of U.S. Pat. No. 5,078,683, granted Jan. 7, 1992, entitled "Programmable Infusion System", and assigned to the assignee hereof, and is incorporated herein by reference as though fully set forth. The heart of the control system is a microcontroller 54, with user interface in the form of a keyboard on the face of the unit, and with motor control for controlling motor 30 for control of flow and various alarm systems. The system has the usual battery and power supply circuit 56, with voltage regulators controlling the supply of power to the microcontroller and to the motor drive circuit 60 for drive of the motor 30.

The microcontroller 54 is preferably a Motorola MC688C11E9, which is pre-programmed for all operational parameters except for certain operator selected parameters. The operator may select and vary certain parameters from the keyboard.

The microcontroller is programmed to operate the motor to open and close the pinch valve for controlling of flow from the infuser 12. The controller operates in response to an occluder sensor 62 for sensing the open condition of the occluder, and a sensor 64 for sensing the closed position of the occluder. The occluder sensors 62 and 64 are hall effect sensors that sense the position of one or more magnets on the finger 36 or other moving portion of the mechanism. For example, the sensor 64 may be positioned, as shown in FIG. 6, to sense the position of a magnet 65 on the finger 26. Sensor 62 may be positioned to sense the position of a magnet 67 on a disk 69 mounted on drive shaft 32 to signal the open position of FIG. 4 (see FIG. 3).

The occluder in the form of the pinch finger pinches the tubing and acts as a valve for controlling the flow therethrough. User interface with the microcontroller is provided by means of a keyboard, including input keys, designed generally at 66, which are located on the face of the unit. These key inputs enable the operator to select duration of infusion and intervals between dosages. It also enables the user to start and stop the unit and do a certain amount of programming.

An LCD display 68 displays information to the user relative to operational parameters and conditions of the unit. A number of monitoring sensing units interface with the microcontroller. These include a battery door sensor 70, a disposable door sensor unit 72 and an occlusion sensor 74. The unit will cease to function with signals from certain of these units. The occlusion sensor 74 may be of the type disclosed in application Ser. No. 07/518,987, and senses an occlusion in the line or tube other than the controlled occlusion by means of the occluder member or finger 26.

A watch dog controller 76 interfaces with the microcontroller for monitoring various operations. Various conditions, such as alarm conditions, are indicated by an audio alarm 78 and by visual alarms 80 and 82, including battery door open and an occlusion in the line. The green LED 82 preferably indicates running of the unit.

The input keys on the front of the unit include an up key 84, a down key 86 and a start/stop key 88. The up key 84 enables the operator to scroll up through the variables for each of the parameters, starting at the lower limit. He selects the desired value of the variable by scrolling to and stopping at that value.

The down key similarly enables the user to scroll through the variables from each of the parameters, starting at the upper limit and stopping at the selected value of that variable.

The start/stop key starts the programming sequence and allows the user to verify or advance to the next parameter. The infusion can be started or stopped also by pressing this key.

The user display 68 gives the programmed information on the top row, and the infusion status on the bottom row. The program parameters, along the top left to right, are the dose cycle time, number of doses and frequency of dose. The bottom left indicates the running time and the bottom right is either run or keep vein open mode (CVO).

Disposed at each side of the input keys are a red LED 90 at the left and a green LED 92 at the right. The green LED is a flashing green light, which indicates that the controller is running.

The red LED has a mode of a flashing red, which indicates that the controller is in an alarmed condition. A constant red light indicates that the controller is an error condition.

The user programming of the controller is done by scrolling through the parameters and pressing the start/stop key. Each parameter can be changed by using the up or down keys to scroll up through the numbers or down through the numbers. To move from one position in the parameter to the next, the user presses the start/stop key, whereby the position of the parameter that the user is at will flash. In order to move to the next parameter, the user presses the start/stop key. At the end, the user will go through a verified sequence to verify the various parameters. He can interrupt the pump and change any of the parameters at any time during a protocol.

The controller is designed to control the flow of an infusion fluid from an infuser to an infusion site of a patient.

Figure 8:
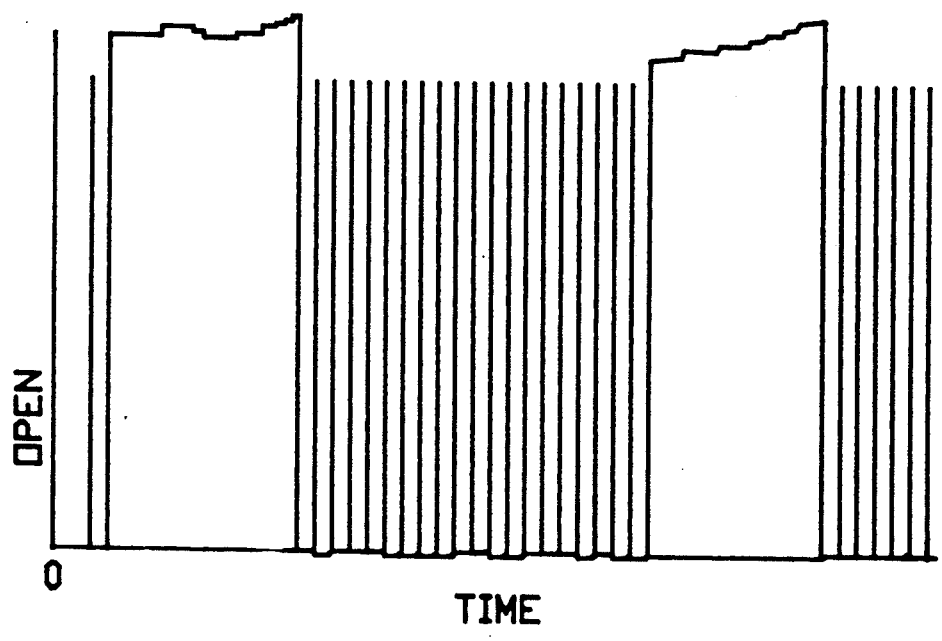
FIG. 8 is a graph of dosages and vein open infusions.

Referring to FIG. 8, the controller is designed to provide multiple doses of selected duration interspersed with a pulse or momentary open of the flow to keep the vein of the user open. As illustrated in FIG. 9 wherein the open position or condition is shown at the upper limit of the vertical, and the time on the horizontal, the keep vein open pulses occur at selected intervals between infusion doses of selected durations interspersed by the KVO mode. For example, it may be programmed to infuse a 100 ml. dose at one hour intervals, with a pulse at about one-tenth of an hour between infusion doses. The single lines represent a pulsed or momentary open condition. The blocks represent a period of infusion of a dose.

The disposable unit 12 is provided with an occlusion drum, which is biased against an occlusion sensor switch in the bottom of the channel at 20. The door 17 pushes the drum 100 against the sensing switch and provides the platen necessary to actuate the occlusion sensor. The door 17 also protects the disposable unit 12 against tampering and the like.

While we have illustrated and described our invention by means of specific embodiments, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

We claim:

1. A multiple dose infusion controller for controlling the delivery of multiple dosages of an intravenous fluid from a source to a site, comprising:

a compact, portable housing having a receptacle slot extending across a face thereof for removably receiving a segment of a disposable tubing means connected to an IV source for transporting an IV fluid to a site;

occlusion valve means mounted in the housing and including a valve member moveable between open and closed conditions, said valve member moveable to said closed condition for periodically engaging and compressing the segment of the disposable tubing means for closing said tubing for selectively preventing flow of fluid therethrough;

power means mounted in the housing for driving the valve member upon energization thereof to a selected one of said open and closed conditions; and control means mounted in the housing programmed for providing multiple selected dosage modes separated by a keep vein open mode over a selected period of time for said modes provided by periodically energizing the power means for selectively starting and stopping the flow of the fluid through the disposable tubing means in accordance with predetermined delivery time and duration parameters for each selected dosage mode and momentarily opening and closing said valve at selected time intervals for said keep vein open mode over a selected period of time between said infusion modes.

2. An infusion controller according to claim 1 wherein said valve member is a finger mounted for reciprocation transverse to the axis of the slot and extends through a side wall thereof.

3. An infusion controller according to claim 2 wherein said slot includes a platen extending outward from a wall opposite said finger.

4. An infusion controller according to claim 2 wherein said power means comprises a rotary motor having a rotary shaft, an eccentric on said shaft drivingly connected to said finger by means of a yoke on said finger.

5. An infusion controller according to claim 1 further comprising an elastic segment of a disposable tubing removably disposed in said receptacle slot.

6. An infusion controller according to claim 5 wherein said valve member is a finger mounted for reciprocation transverse to the axis of the slot and extends through a side wall thereof.

7. An infusion controller according to claim 6 wherein said slot includes a platen extending outward from a wall opposite said finger.

8. An infusion controller according to claim 7 wherein said power means comprises a rotary motor having a rotary shaft, an accentric on said shaft in driving engagement with a yoke on said finger.

9. An infusion controller according to claim 8 wherein said eccentric includes high lift and low lift spots and flat surfaces at the high lift and low lift spots of said eccentric, and biasing means for biasing said yoke against said surfaces for latching said finger in a selected one of an open and a closed condition.

10. A multiple dose infusion controller for selectively delivering multiple dosages of an intravenous fluid from a source to a patient, comprising:

disposable tubing means connected at one end to a source of IV fluid and having means at the other end for connection to an injection site of a patient for conveying intravenous fluid from a source to a patient, said tubing means having an intermediate elastic segment;

a compact, portable housing having an open receptacle slot extending across a face thereof for removably receiving said elastic segment of said disposable tubing means;

reciprocating finger means mounted in the housing for periodically engaging and compressing the elastic segment of the disposable tubing means for closing said tubing for preventing flow of fluid therethrough, thereby providing fully open and fully closed conditions of said tubing;

motor means mounted in the housing for driving the finger means to a selected one of fully open and fully closed conditions upon energization thereof; and control means mounted in the housing and programmed for providing multiple selected dosage modes separated by a keep vein open mode over a selected period of time, said modes provided by controllably energizing the motor means for selectively controlling the flow of the fluid through the disposable means in accordance with predetermined delivery time and duration parameters for each selected dosage mode and momentarily opening and closing said valve at selected time intervals for said keep vein open mode over a selected period of time between said dosage modes.

11. An infusion controller according to claim 10 wherein said power means comprises a rotary motor having a rotary shaft, an eccentric on said shaft in driving engagement with a yoke on said finger.

12. An infusion controller according to claim 11 wherein said eccentric includes high and low lift spots and flat surfaces at the high lift and low lift spots of said eccentric, and biasing means for biasing said yoke against said surfaces for latching said finger in a selected one of an open and closed condition.

13. An infusion controller according to claim 12 wherein said control means includes keypad means mounted in the housing for enabling the user to send commands to the control means.

14. A multiple dose infusion system having a controller for selectively delivering multiple dosages of an intravenous fluid from a source to a patient, comprising in combination:

an inflatable bladder infusion apparatus for containing an IV fluid under pressure;

disposable tubing means connected at one end to said infusion apparatus and having means at the other end for connection to an injection site of a patient for conveying intravenous fluid from said infusion apparatus to a patient, said tubing means having an intermediate elastic segment;

a compact, portable housing having an open receptacle slot extending across a face thereof for removably receiving said elastic segment of said disposable tubing means;

reciprocating finger means mounted in the housing for periodically engaging and compressing the elastic segment of the disposable tubing means for closing said tubing for preventing flow of fluid therethrough;

a rotary motor having a shaft mounted in the housing, and an eccentric on said shaft in driving engagement with a yoke on said finger for driving the finger upon energization thereof selectively into and out of engagement with the elastic segment for defining closed and open conditions of said elastic segment, said eccentric includes high and low lift spots and flat surfaces at the high lift and low lift spots of said eccentric, and a compression spring biasing said yoke against said surfaces for latching said finger in a selected one of an open and a closed condition; and control means mounted in the housing for controllably energizing the motor means for selectively opening and closing said elastic segment for controlling the flow of the fluid through the disposable means in accordance with predetermined delivery time and duration parameters for providing multiple selected dosage modes separated by a keep vein open mode.

* * * * *